(12) United States Patent
Schon et al.

(10) Patent No.: US 9,752,814 B2
(45) Date of Patent: Sep. 5, 2017

(54) COOLING APPARATUS USED FOR CRYONIC PRESERVATION, AND CORRESPONDING OPERATING METHOD

(71) Applicant: Fraunhofer-Gesellschaft zur Foerderung der angewandten Forschung, e.V., Munich (DE)

(72) Inventors: Uwe Schon, Neunkirchen (DE); Heiko Zimmermann, Kronberg im Taunus (DE); Guenter Fuhr, Berlin (DE)

(73) Assignee: FRAUNHOFER-GESELLSCHAFT ZUR FORDERUNG DER ANGEWANDTEN FORSCHUNG, E.V., Munich (DE)

( * ) Notice: Subject to any disclaimer, the term of this patent is extended or adjusted under 35 U.S.C. 154(b) by 284 days.

(21) Appl. No.: 14/047,570

(22) Filed: Oct. 7, 2013

(65) Prior Publication Data

US 2014/0033739 A1  Feb. 6, 2014

Related U.S. Application Data

(63) Continuation of application No. 10/595,308, filed as application No. PCT/EP2004/011172 on Oct. 6, 2004, now Pat. No. 8,584,473.

(30) Foreign Application Priority Data

Oct. 8, 2003 (DE) .................... 103 46 793

(51) Int. Cl.
  *F25D 3/10* (2006.01)
  *A01N 1/02* (2006.01)
  (Continued)

(52) U.S. Cl.
  CPC ............. *F25D 3/10* (2013.01); *A01N 1/02* (2013.01); *A01N 1/0257* (2013.01);
  (Continued)

(58) Field of Classification Search
  CPC ...... F17C 9/02; F17C 7/00; F17C 9/00; F25D 25/00; F25D 3/11; F25D 25/04;
  (Continued)

(56) References Cited

U.S. PATENT DOCUMENTS 3,092,974 A  6/1963  Haumann et al.
3,245,248 A  4/1966  Ritter
(Continued)

FOREIGN PATENT DOCUMENTS

DE  8807267  9/1988
DE  4023573  7/1991
DE  10229864  3/2003

*Primary Examiner* — Dominick L Plakkoottam
*Assistant Examiner* — Meraj A Shaikh
(74) *Attorney, Agent, or Firm* — Caesar Rivise, PC

(57) ABSTRACT

The invention relates to a cooling apparatus, especially for cryogenically preserving biological samples, including a duct (5) for delivering a coolant (3) to a cooling chamber (1), a heater (6) that has an adjustable first heating performance (P2) for heating the coolant (3) delivered to the cooling chamber (1), a first temperature sensor (8-10) for measuring the temperature (T2-T4) in the cooling chamber (1), a second temperature sensor (7) for measuring the temperature (Ti) of the coolant (3) delivered to the cooling chamber (I), and a regulator (11) for regulating the temperature. The regulator (11) is embodied as a multiple regulator which detects several temperatures (T1-T4) as control variables and/or adjusts several heating performances (P1, P2) as manipulated variables. The invention further relates to a corresponding operating method.

26 Claims, 4 Drawing Sheets

(51) Int. Cl.
  *F25D 29/00* (2006.01)
  *G01N 1/42* (2006.01)
  *B01L 7/00* (2006.01)

(52) U.S. Cl.
  CPC ............ *F25D 29/001* (2013.01); *G01N 1/42* (2013.01); *B01L 7/00* (2013.01); *F25D 2700/12* (2013.01)

(58) Field of Classification Search
  CPC .. F25D 17/042; F25D 2317/0415; F24F 3/14; F24F 3/153; F24F 6/00; F24F 2006/008; G05D 21/00
  USPC ......... 62/50.2, 62, 63, 78, 92, 93, 48.1, 173, 62/177, 417; 236/44 C; 261/140.1, 30, 261/128, 130, 152
  See application file for complete search history.

(56) References Cited

U.S. PATENT DOCUMENTS

| | | | |
|---|---|---|---|
| 3,267,585 A | | 8/1966 | Futer |
| 3,595,030 A | | 7/1971 | Roslonski |
| 4,107,937 A | * | 8/1978 | Chmiel ................. F25D 29/001 165/290 |
| 4,397,158 A | * | 8/1983 | Brenik .................... B29C 35/16 62/380 |
| 4,566,283 A | * | 1/1986 | Boese ....................... F17C 9/02 62/49.2 |
| 5,003,787 A | | 4/1991 | Zlobinsky |
| 5,048,300 A | | 9/1991 | Lihl |
| 5,335,503 A | * | 8/1994 | Lee ....................... F25D 29/001 62/239 |
| 5,779,981 A | * | 7/1998 | Danssaert ................. B01L 7/52 422/552 |
| 6,065,294 A | * | 5/2000 | Hammerstedt ........... F25D 3/10 422/65 |
| 6,178,757 B1 | * | 1/2001 | Sitte ...................... F25D 29/001 165/206 |
| 6,389,828 B1 | * | 5/2002 | Thomas .............. B29C 47/0016 264/237 |
| 7,031,154 B2 | * | 4/2006 | Bash .................. H05K 7/20736 165/80.3 |
| 2003/0029179 A1 | | 2/2003 | Vander Woude et al. |

\* cited by examiner

COOLING APPARATUS USED FOR CRYONIC PRESERVATION, AND CORRESPONDING OPERATING METHOD

BACKGROUND OF THE INVENTION

The invention relates to cooling equipment, especially for the cryopreservation of biological samples.

The freezing of biological samples such as, e.g., stem cells in order to preserve their vitality is known within the scope of so-called cryopreservation. A cooling down to less than −130° C. is necessary here for a complete preservation of vitality so that liquid nitrogen is usually used as cooling agent. However, not only the low storage temperature is important for the preservation of vitality but also the observance of a given temperature course in time during freezing and thawing.

In order to meet these requirements, cooling equipment is obtainable, e.g., from DE 88 07 267.3 that uses liquid nitrogen with a boiling point of −196° C. as cooling agent. The liquid nitrogen is at first located in a cooling agent storage container and is heated in it by an electrically operated evaporator, the outgassing nitrogen being conducted via a cooling agent supply line into a cooling chamber and correspondingly cools its inner space so that material to be cooled located in the cooling chamber is frozen.

However, the mere outgassing of nitrogen by the evaporator only makes cooling agent temperatures near the boiling point of −196° C. possible, whereas, on the other hand, the cooling chamber should also be cooled to higher temperatures, especially during the freezing and thawing. Therefore, an electrically operated heater that heats the outgassing nitrogen to the desired temperature is arranged in the cooling agent supply line between the cooling agent storage container and the cooling chamber.

Furthermore, the known cooling equipment comprises a control device that measures the temperature of the cooling agent introduced into the cooling chamber as a control variable and adjusts the heating performance of the heater arranged in the cooling agent supply line as a manipulated variable in order to achieve the desired temperature course in time during freezing and thawing. Thus, the control device controls only a single heater and evaluates only a single temperature.

However, the previously described, known cooling equipment has the disadvantage of an unsatisfactory control behavior, which expresses itself in an overswinging between the target temperature and the actual temperature and results in a deviation from the desired temperature course in time during freezing and thawing. As a result, the unsatisfactory control behavior of the known cooling equipment can result in damage to the biological samples to be preserved.

The invention therefore has the task of improving the temperature control behavior in the previously described, known cooling equipment.

SUMMARY OF THE INVENTION

The invention comprises the general technical teaching of detecting not only the temperature in the cooling chamber but also at least one other temperature such as, e.g., the temperature of the heated cooling agent supplied to the cooling chamber as control variables.

Furthermore, the invention also comprises the general technical teaching of adjusting at least one further manipulated variable such as, e.g., the heating performance of the evaporator arranged in the cooling agent storage container in addition to the heating performance of the heater arranged in the cooling agent supply line.

Therefore, the cooling equipment of the invention preferably has a multiple controller that detects several temperatures as control variables and/or adjusts several heating performances as manipulated variables. The concept of a multiple controller used here is to be understood in a general manner and not limited to a single controller that has several inputs and/or several outputs, but it is also possible that the multiple controller comprises two substantially separate control circuits.

Thus, for example, one control circuit can detect the temperature in the cooling chamber as a control variable and adjust the heating performance of the evaporator as a manipulated variable while another control circuit detects the temperature of the heated cooling agent prior to its introduction into the cooling chamber as a control variable and adjusts the heating performance of the heater arranged in the cooling agent supply line as a manipulated variable.

If the actual temperature in the cooling chamber is above the target temperature, the heating performance of the evaporator is increased so that more nitrogen outgases and passes into the cooling chamber, which results in a correspondingly greater cooling.

On the other hand, if the actual temperature in the cooling chamber is less than the target temperature, the heating performance of the evaporator is reduced in order that less nitrogen outgases. This down-regulation of the evaporator when the cooling is sufficient also has the advantage that nitrogen is not consumed unnecessarily.

The controlling of the heating performance of the heater arranged in the cooling agent supply line takes place in a similar manner in that this heating performance is increased when the actual temperature of the heated cooling agent is below the target temperature in the cooling chamber. In a corresponding manner, the heating performance of the heater arranged in the cooling agent supply line is reduced if the actual temperature of the heated cooling agent is above the target temperature in the cooling chamber.

In a preferred exemplary embodiment of the invention the measuring of the temperature in the cooling chamber does not take place by a single temperature sensor but rather by several temperature sensors that are preferably arranged in a spatially distributed manner in order to be able to detect local temperature variations within the cooling chamber. The control device can then takes into account the formation of local temperature peaks within the cooling chamber by forming an average value and supplying documentation about the actual temperature distribution.

It is furthermore advantageous if at least one temperature sensor has a thermocouple whereas another temperature sensor is designed as a temperature-dependent electrical resistor. Such a combination of different sensor types is appropriate since in this manner the advantages of the different sensor types can be utilized and the disadvantages are avoided. Thus, thermocouples have a good dynamic behavior as temperature sensors but the accuracy is relatively low. On the other hand, temperature-dependent electrical resistors have a poor dynamic behavior due to their thermal inertia but have great accuracy. Thus, the temperature can be measured very dynamically and very accurately by a combination of these two sensor types.

For example, so-called NTC's (negative temperature coefficients) or PTC's (positive temperature coefficients) can be used as temperature-dependent electrical resistors.

Furthermore, the cooling equipment of the invention preferably has a storage equipment in order to record the temperature in the cooling chamber and/or the temperature of the heated cooling agent before it enters into the cooling chamber. For example, a commercial PC that is connected via a data interface to the control device of the cooling equipment according to the invention can be used for this. Furthermore, such a PC can also assume the task of setting the desired temperature courses in time during freezing and thawing.

It is furthermore desirable in the cryopreservation of biological samples to avoid spatial temperature fluctuations within the cooling chamber in order that a defined freezing or thawing is possible independent of the positioning of the biological sample to be preserved within the cooling chamber. In the preferred exemplary embodiment of the invention, the cooling agent supply line therefore empties via a diffuser into the cooling chamber, the diffuser distributing the cooling agent that is streaming in as uniformly as possible in the cooling chamber. Such a diffuser can consist, e.g., of an antechamber into which the cooling agent is first introduced, the antechamber being connected over a large area via outlets to the cooling chamber in order to avoid local temperature influences.

In a variant of the invention, the cooling agent supply line empties laterally and preferably only on one side of the cooling chamber into the cooling chamber. This is advantageous since streams of cooling agents then form inside the cooling chamber that rapidly result in a thorough mixing and a temperature adjustment.

In contrast thereto, in another variant of the invention the cooling agent supply line empties on the top of the cooling chamber into the cooling chamber, which can be particularly advantageous if the cooling chamber is a cooling bell open on the bottom.

The concept of a cooling chamber cited here is therefore not limited to stationary cooling chambers into which the cooled material is introduced, but it is also possible that the cooling chamber is a mobile cooling bell that is placed on the particular cooled material.

It should also be mentioned that the invention is not limited to nitrogen as cooling agent but it is also possible within the framework of the invention to use other cooling agents such as, e.g., air or helium.

In addition, the invention also comprises a corresponding operating method for such a cooling equipment.

BRIEF DESCRIPTION OF SEVERAL VIEWS OF THE DRAWINGS

Other advantageous further developments of the invention are explained in detail in the following together with the description of the preferred exemplary embodiments of the invention using the figures.

DETAILED DESCRIPTION OF PREFERRED EMBODIMENTS

Figure 1:
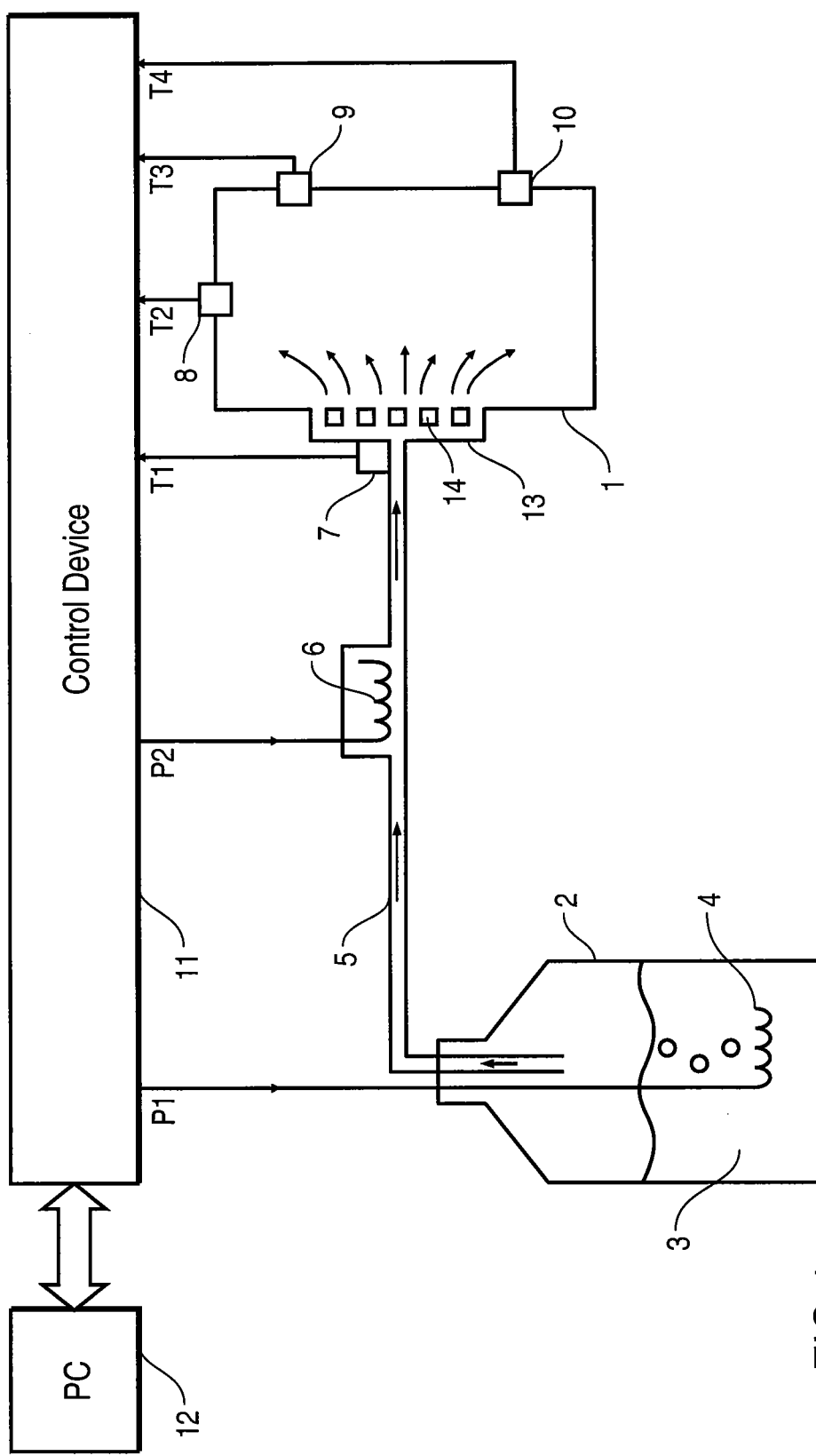
FIG. 1 shows a schematic view of a cooling equipment in accordance with the invention for the cryopreservation of biological samples.

The cooling equipment shown in FIG. 1 serves the vitality-preserving cryopreservation of biological samples in which the samples are frozen and thawed in a cooling chamber 1.

In addition, the cooling equipment has a cooling agent storage container 2 in which liquid nitrogen is present as cooling agent 3, where the cooling agent 3 can be evaporated by an electrically operated evaporator 4.

The cooling agent 3 outgassing into the cooling agent storage container 2 with a temperature close to the boiling point of $-196°$ C. then passes via a cooling agent supply line 5 into the cooling chamber 1, which results in a corresponding cooling.

The evaporator 4 has an adjustable heating performance P1 in this instance in order to be able to vary the intensity of the cooling. Thus, a large amount of the cooling agent 3 outgasses at a high heating performance P1 of the evaporator, which results in a corresponding, strong cooling action. On the other hand, less of the cooling agent 3 outgasses at a low heating performance P1 of the evaporator 4 so that the cooling action is less as well.

In addition, in order to temper the cooling chamber 1, a heater 6 with an adjustable heating performance P2 is provided, the heater 6 being arranged in the cooling agent supply line 5 and the heating cooling agent 3 outgassing from the cooling agent storage container 2 prior to its entrance into the cooling chamber 1 in order to achieve temperatures above the boiling point of $-196°$ C., in particular during the freezing and thawing.

Four temperature sensors 7-10 are provided for monitoring the temperature, the temperature sensor 7 measuring a temperature value T1 that reproduces the temperature of the cooling agent 3 heated by the heater 6 before its entrance into the cooling chamber 1.

In contrast thereto, temperature sensors 8-10 measure temperature values T2, T3 and T4 that reproduce the temperature inside the cooling chamber 1 at different points.

The temperature sensors 8-10 are arranged in a spatially distributed manner so that local temperature peaks in the cooling chamber 1 can be compensated by a formation of an average value.

A control device equipment 11 is provided for temperature control here, that detects temperatures T1-T4 as control variables and adjusts the heating performance P1 of the evaporator 4 and the heating performance P2 of the heater 6 as manipulated variables in order to maintain a desired temperature course in time during freezing and thawing, where the temperature course can be given by a conventional PC 12 connected to the control device 11 via a data interface. In addition, the PC 12 also records the temperature values T1-T4 measured by the temperature sensors 7-10 and stores them for subsequent evaluation.

It should further be mentioned that the cooling agent supply line 5 does not empty directly into the cooling chamber 1 but rather indirectly via an antechamber 13 in order to avoid spatial temperature variations in the cooling chamber 1. To this end, the antechamber has a diffuser 4 at the transition to the cooling chamber 1 that results in a turbulence of the cooling agent 3 entering into the cooling chamber 1. Furthermore, the discharge cross section of the antechamber 13 is substantially larger at the transition to the cooling chamber 1 than the entrance cross section at the transition from the cooling agent supply line 5 to the antechamber 13, so that the introduction of the cooling agent into the cooling chamber 1 takes place over a relatively large area.

Figure 3:
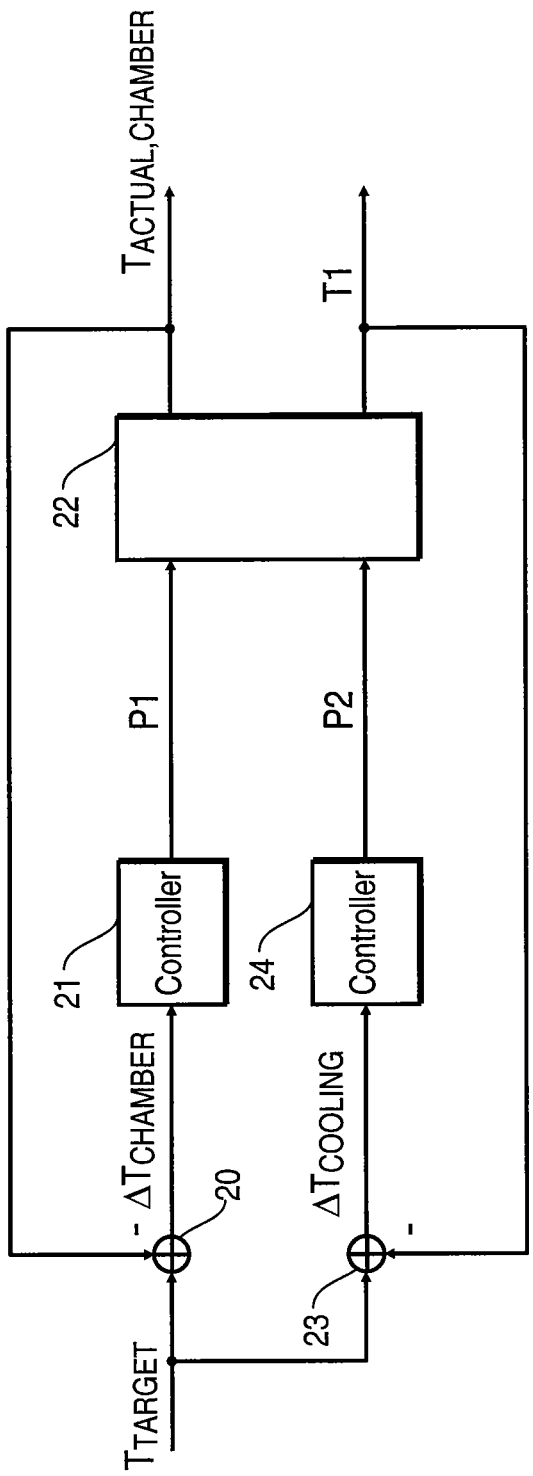
FIG. 3 shows a control-engineering equivalent circuit diagram of the cooling equipment in accordance with the invention.

The temperature control behavior of the control device 11 is described in the following using the control-engineering equivalent circuit diagram shown in FIG. 3.

Thus, the PC 12 constantly sets a target temperature $T_{TARGET}$, that is compared with an actual temperature $T_{ACTUAL,CHAMBER}$ by a subtracter 20, the actual temperature $T_{ACTUAL,CHAMBER}$ being calculated as the average value of temperatures T2, T3 and T4.

The subtracter 20 calculates a target-actual deviation $\Delta T_{CHAMBER}$ from the target temperature $T_{TARGET}$ and the actual temperature $T_{ACTUAL,CHAMBER}$ and conducts it to a controller 21 that correspondingly adjusts the heating performance P1 of the evaporator 4.

Furthermore, the control-engineering equivalent circuit diagram shows a controlled system 22 that reacts to the heating performance P1 of the evaporator 4 and the heating performance P2 of the heater 6 so that the actual temperature $T_{ACTUAL,CHAMBER}$ is adjusted.

In addition to the previously described control circuit for the evaporator 4, the control device 11 has another control circuit for adjusting the heating performance P2 of the heater 6.

Thus, the target temperature $T_{TARGET}$ for the temperature inside the cooling chamber 1 is supplied to another subtracter 23 that compares the target temperature $T_{TARGET}$ with the actual temperature T1 of the heated cooling agent. The subtracter 23 calculates a target-actual deviation $\Delta T_{COOLING\ AGENT}$ from the above and supplies it to another controller 24 that appropriately adjusts the heating performance P2 of the heater 6, whereupon the controlled system 22 reacts in an appropriate manner so that the actual temperature T1 is adjusted.

The controller 24 controls the heating performance P2 of the heater 6 in such a manner in this instance that the actual temperature T1 of the cooling agent 3 supplied to the cooling chamber 1 corresponds to the extent possible to the target temperature $T_{TARGET}$ in the cooling chamber 1.

Figure 2:
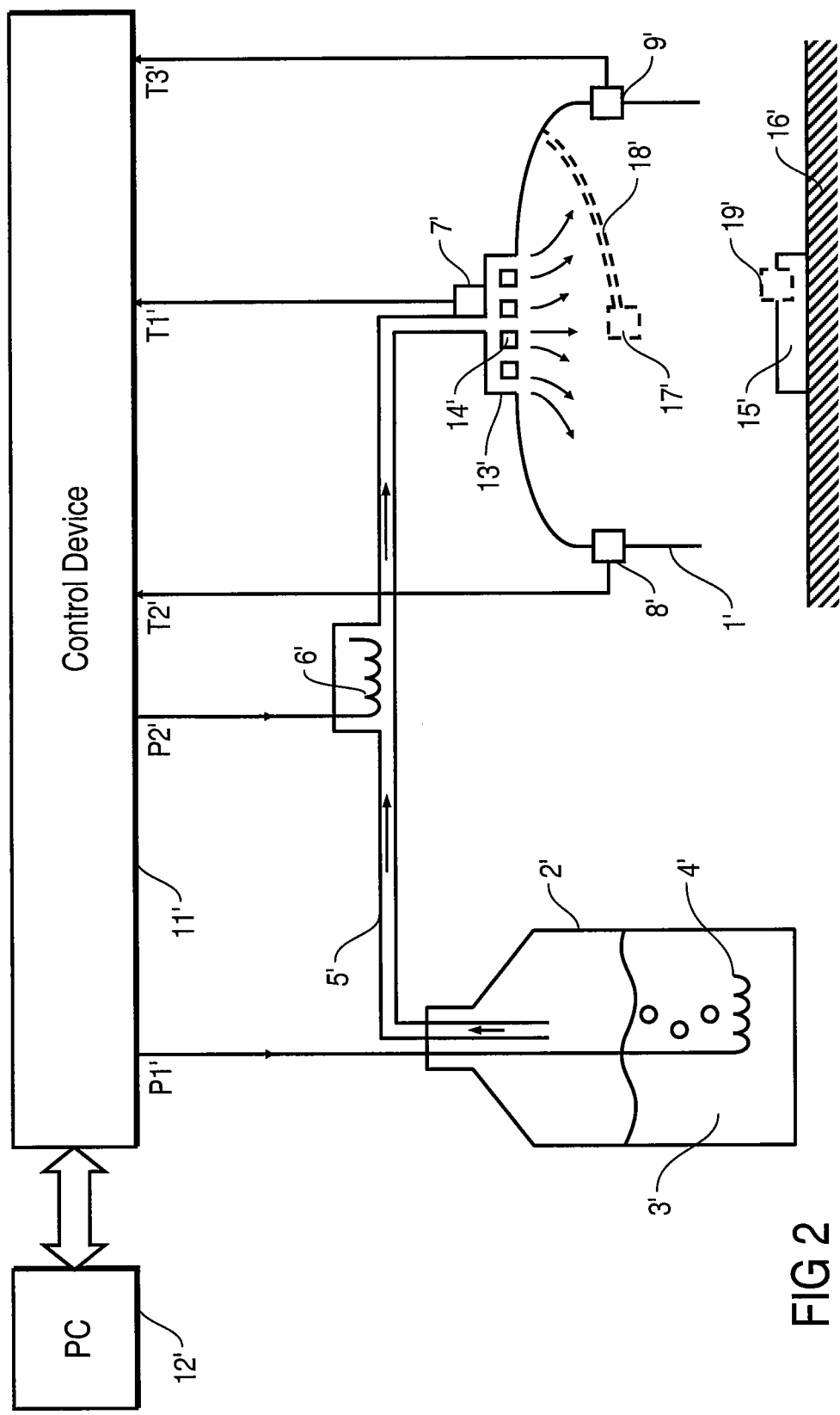
FIG. 2 shows an alternative exemplary embodiment of a cooling equipment in accordance with the invention.

The exemplary embodiment shown in FIG. 2 largely corresponds to the previously described exemplary embodiment shown in FIG. 1, so that in order to avoid repetitions, reference is made to the previous description for FIG. 1 and the same reference signs are used in the following for corresponding structural components, that are characterized by an apostrophe solely in order to distinguish them.

A particularity of this exemplary embodiment consists in the fact that the cooling chamber 1' is designed to be open on its bottom and bell-shaped. Thus, the cooling chamber 1' is mobile in this instance and can therefore be placed on a biological sample 15' to be frozen, the sample 15' resting on a solid base 16' such as, e.g., a laboratory table. The cooling agent supply line 5' is therefore flexible in this exemplary embodiment in order to make a flexible handling of the cooling chamber 1' possible.

Another difference of this exemplary embodiment from the exemplary embodiment shown in FIG. 1 is that the cooling agent supply line 5' empties into the cooling chamber 1' at the top of the cooling chamber 1'.

Moreover, the cooling equipment in this exemplary embodiment can have another temperature sensor 17' attached in the cooling chamber 1' by a holding arm 18'. The holding arm 18' positions the temperature sensor 17' inside the cooling chamber 1' at the location at which the sample 15' is located when the cooling chamber 1' is placed on the base 16'. In this manner, the temperature sensor 17' very accurately measures the local temperature at the location of the sample 15', which makes a very accurate temperature control possible.

Furthermore, a temperature sensor 19' can be arranged directly on the sample 15' or a support carrying the sample 15' in this exemplary embodiment, which makes an even more accurate measuring of the sample temperature possible since local temperature variations in the cooling chamber 1' are not taken into consideration.

The transmission of the temperature measured by the temperature sensor 19' to the control device 11' can take place, e.g., by traditional electrical lines. However, it is basically also possible to transmit the temperature measured by the temperature sensor 19' in a wireless manner to the control device 11'. The mobility and portability of the cooling chamber 1' is not adversely affected by such a wireless transmission. The wireless transmission of the measured temperature can take place, e.g., by a transponder integrated in the temperature sensor 19' or in a sample carrier. There are multiple known possibilities here as regards the transmission type such as, e.g., radio transmission, ultrasonic transmission, optical transmission, in particular infrared transmission, etc.

Figure 4:
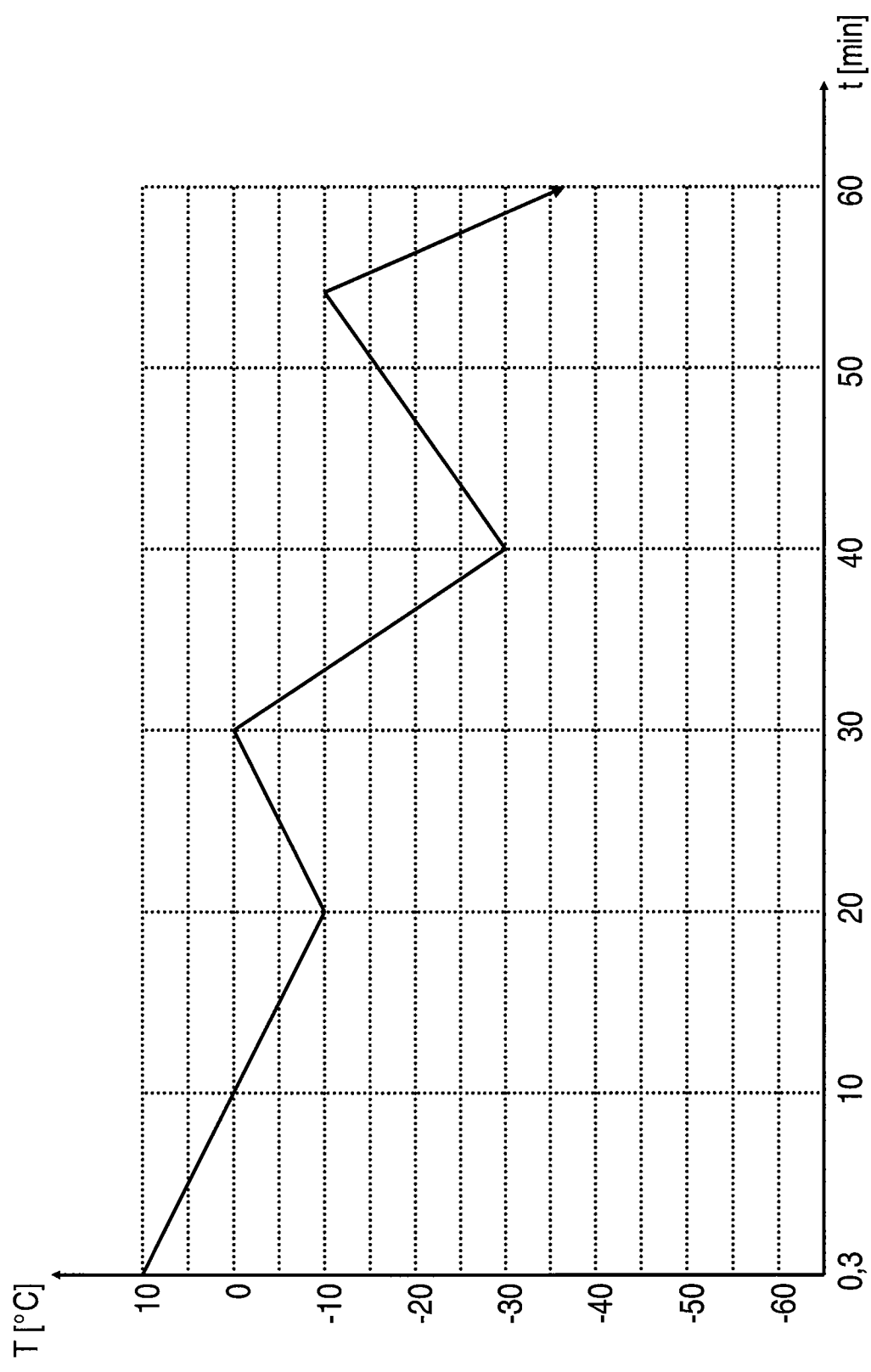
FIG. 4 shows a temperature course in time in the cooling chamber during the freezing of biological samples.

Finally, FIG. 4 shows a typical temperature course in time in cooling chamber 1 during the freezing of a biological sample within the framework of cryopreservation. It is apparent from it that several cooling and warming phases are successively passed through during freezing in order to freeze the biological samples while preserving as much vitality as possible.

However, any desired cooling and warming phases are possible within the framework of the invention, where the time of the individual phases and the cooling and warming temperature can be set as desired.

The invention is not limited to the preferred exemplary embodiments previously described, but rather a plurality of variants and modifications are possible that also make use of the concept of the invention and therefore fall within its protective range.

LIST OF REFERENCE SIGNS 1, 1' cooling chamber
2, 2' cooling agent storage container
3, 3' cooling agent
4, 4' evaporator
5, 5' cooling agent supply line
6, 6' heater
7, 7' temperature sensor
8, 8' temperature sensor
9, 9' temperature sensor
10, 10' temperature sensor
11, 11' control device
12, 12' PC
13, 13' antechamber
14, 14' diffuser
15' sample
16' base
17' temperature sensor
18' holding arm
19' temperature sensor
20 subtracter
21 controller
22 controlled system
23 subtracter
24 controller
P1, P1' heating performance of the evaporator P2, P2' heating performance of the heater
T1, T1' temperature of the heated cooling agent
T2-T4, T2', T3' temperature inside the cooling chamber

What is claimed is:

1. Cooling equipment, comprising:
   a) a cooling agent storage container housing a cooling agent;
   b) a non-recirculating cooling chamber;
   c) a cooling agent supply line connected to the cooling agent storage container for supplying the cooling agent to the non-recirculating cooling chamber;
   d) an antechamber in fluid communication between the cooling agent supply line and the cooling chamber, said antechamber including a diffuser spatially diffusing the cooling agent directly from the cooling agent supply line into distinct channels for supply to the cooling chamber;
   e) a heater with an adjustable first heating performance for heating the cooling agent supplied to the cooling chamber, wherein the heater is integrated in the cooling agent supply line;
   f) an evaporator in the cooling agent storage container with an adjustable second heating performance for evaporating the cooling agent present in the cooling agent storage container;
   g) a first temperature sensor for measuring the temperature in the cooling chamber;
   h) a second temperature sensor for measuring an agent temperature of the cooling agent supplied to the cooling chamber; and
   i) a controller for temperature control, the controller having an input side and an output side, the input side connected to the first temperature sensor and the second temperature sensor, the output side connected to the heater and the evaporator, wherein the controller:
      (i) is adapted to detect several temperatures from said first temperature sensor and said second temperature sensor as control variables;
      (ii) is a multiple controller; and
      (iii) adjusts said first heating performance and said second heating performance as manipulated variables based on said temperatures detected by said first temperature sensor and said second temperature sensor;
   wherein said multiple controller includes:
   a first control circuit that detects temperature from the first temperature sensor in the cooling chamber as a first control variable and adjusts said adjustable second heating performance of the evaporator as a first manipulated variable based on the first control variable; and
   a second control circuit that detects temperature from the second temperature sensor measuring temperature of the cooling agent before entering the cooling chamber as a second control variable and adjusts said adjustable first heating performance of the heater as a second manipulated variable based on the second control variable;
   wherein the heater is between the evaporator and the first temperature sensor, and the first temperature sensor controls the evaporator; and
   wherein the second temperature sensor is between the evaporator and the first temperature sensor, and the second temperature sensor controls the heater.

2. The cooling equipment according to claim 1, wherein several temperature sensors connected to the controller are provided for measuring the chamber temperature in the cooling chamber.

3. The cooling equipment according to claim 2, wherein the temperature sensors are arranged in a spatially distributed manner for measuring a spatial distribution of temperature.

4. The cooling equipment according to claim 2, wherein at least one of the temperature sensors is a thermocouple and at least one of the temperature sensors is a temperature-dependent electrical resistor.

5. The cooling equipment according to claim 1, wherein the cooling agent is nitrogen.

6. The cooling equipment according to claim 1, wherein the first temperature sensor and the second temperature sensor are connected to storage equipment that stores temperature courses.

7. The cooling equipment according to claim 1, wherein the cooling agent supply line is adapted to empty via the diffuser into the cooling chamber.

8. The cooling equipment according to claim 1, wherein the cooling agent supply line is adapted to empty laterally into the cooling chamber.

9. The cooling equipment according to claim 8, wherein the cooling agent supply line is adapted to empty into the cooling chamber only on one side of the cooling chamber.

10. The cooling equipment according to claim 1, wherein the cooling agent supply line is adapted to empty into the cooling chamber at the top of the cooling chamber.

11. The cooling equipment according to claim 1, wherein the cooling chamber is closed.

12. The cooling equipment according to claim 1, wherein the cooling chamber is open on its bottom.

13. The cooling equipment according to claim 1, wherein the cooling chamber is portable.

14. The cooling equipment according to claim 1, wherein the first temperature sensor is arranged inside the cooling chamber and at an interval from a wall of the cooling chamber.

15. The cooling equipment according to claim 14, wherein the first temperature sensor is fastened to the cooling chamber by holding equipment extending into the cooling chamber.

16. The cooling equipment according to claim 14, wherein the first temperature sensor is attached to a sample or to a sample holder.

17. The cooling equipment according to claim 1, wherein the first temperature sensor is connected to a transponder that transmits a measured temperature in a wireless manner to the controller.

18. The cooling equipment according to claim 17, wherein the transponder is selected from the group consisting of a radio transponder, an ultrasonic transponder, an optical transponder and an infrared transponder.

19. An operating method for cooling equipment, said method comprising:
   a) introducing a cooling agent from a cooling agent supply line into a non-recirculating cooling chamber for cooling cooled material, the introducing step including spatially diffusing the cooling agent directly from the cooling agent supply line into distinct channels for supply of the cooling agent to the non-recirculating cooling chamber via a diffuser of an antechamber in fluid communication between the cooling agent supply line and the non-recirculating cooling chamber;
   b) heating with a heater the cooling agent prior to the introducing step with an adjustable first heating performance;
   c) measuring an agent temperature of the heated cooling agent prior to being supplied to the cooling chamber;

d) measuring of a chamber temperature in the non-recirculating cooling chamber; and e) controlling the agent temperature and the chamber temperature in that both temperatures are detected as control variables, including controlling the adjustment of a second heating performance of said cooling agent prior to heating in step b) as another manipulated variable in addition to controlling of the first heating performance based on said measured agent temperature and said measured chamber temperature;

wherein step e) includes the steps of:

detecting temperature in the cooling chamber as a first control variable and adjusting heating performance of an evaporator in a cooling agent storage container that supplies the cooling agent to the cooling chamber as a first manipulated variable based on the first control variable; and detecting temperature of the cooling agent after leaving the cooling agent storage container and before entering the cooling chamber as a second control variable and adjusting the heating in step b) as a second manipulated variable based on the second control variable, wherein the heating is after the cooling agent storage container;

wherein the heater is between the evaporator and a first temperature sensor that detects temperature in the cooling chamber, and the first temperature sensor controls the evaporator; and wherein a second temperature sensor that detects temperature of the cooling agent after leaving the cooling agent storage container and before entering the cooling chamber is between the evaporator and the first temperature sensor, and the second temperature sensor controls the heater.

20. The operating method according to claim 19, further comprising the following steps:

f) evaporating the liquid cooling agent in a cooling agent storage container with an adjustable second heating performance to provide an evaporated cooling agent;

g) heating the evaporated cooling agent prior to the introducing step with the adjustable first heating performance; and h) multiple controlling of the first heating performance and of the second heating performance.

21. The operating method according to claim 19, further comprising the following steps:

f) measuring of several spatially distributed temperatures inside the cooling chamber; and g) multiple controlling of the first heating performance and of the second heating performance as a function of the different temperatures inside the cooling chamber.

22. The operating method according to claim 19, further comprising the following steps:

f) measuring with a thermocouple the chamber temperature and the agent temperature prior to the introducing step;

g) measuring with a temperature-dependent resistor the chamber temperature and the agent temperature prior to the introducing step; and h) multiple controlling of the first heating performance and of the second heating performance as a function of temperatures measured by the thermocouple and of temperatures measured by the temperature-dependent resistor.

23. The operating method according to claim 19, further comprising the following steps:

f) setting a target value in the cooling chamber, g) controlling the agent temperature of the cooling agent entering into the cooling chamber in accordance with the target value set for the cooling chamber by adjusting the first heating performance.

24. The operating method according to claim 23, wherein the agent temperature of the cooling agent entering into the cooling chamber is controlled to the target value for the chamber temperature in the cooling chamber.

25. A method of cryopreserving a biological sample comprising cooling the biological sample in the cooling equipment according to claim 1.

26. The cooling equipment according to claim 1, wherein the second temperature sensor measures temperature at a location before the cooling chamber and after the evaporator.

* * * * *